US011439593B2

(12) United States Patent
Krainbring

(10) Patent No.: US 11,439,593 B2
(45) Date of Patent: *Sep. 13, 2022

(54) COMPOSITION FOR TREATING ONYCHOMYCOSIS

(71) Applicant: NCP NewCare Products GmbH, Quickborn (DE)

(72) Inventor: Volker Gustav Adolf Krainbring, Quickborn (DE)

(73) Assignee: NCP NewCare Products GmbH, Quickborn (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/766,822

(22) PCT Filed: Nov. 20, 2018

(86) PCT No.: PCT/EP2018/081857
§ 371 (c)(1),
(2) Date: May 26, 2020

(87) PCT Pub. No.: WO2019/105793
PCT Pub. Date: Jun. 6, 2019

(65) Prior Publication Data
US 2021/0015747 A1    Jan. 21, 2021

(30) Foreign Application Priority Data
Dec. 1, 2017  (EP) .................... 17204960

(51) Int. Cl.
*A61K 9/107* (2006.01)
*A61K 9/00* (2006.01)
*A61K 45/00* (2006.01)
*A61K 47/10* (2017.01)
*A61K 47/18* (2017.01)
*A61K 47/20* (2006.01)
*A61K 47/26* (2006.01)

(52) U.S. Cl.
CPC .......... *A61K 9/1075* (2013.01); *A61K 9/0014* (2013.01); *A61K 45/00* (2013.01); *A61K 47/10* (2013.01); *A61K 47/18* (2013.01); *A61K 47/20* (2013.01); *A61K 47/26* (2013.01)

(58) Field of Classification Search
CPC ....... A61K 47/20; A61K 9/1075; A61K 47/10
See application file for complete search history.

(56) References Cited

U.S. PATENT DOCUMENTS 6,121,214 A * 9/2000 Exner .................. A61K 8/39
510/130
2006/0216251 A1 9/2006 Morariu 2007/0003582 A1 1/2007 Heng
2008/0153748 A1* 6/2008 Jaynes .................. A61K 38/10
514/3.3
2009/0068255 A1 3/2009 Yu et al.
2013/0202540 A1 8/2013 Heng
2016/0120803 A1* 5/2016 Mathur .................. A61K 31/56
514/169
2016/0206536 A1 7/2016 Lewis, II et al.
2017/0189326 A1 7/2017 Perricone et al.
2018/0353410 A1* 12/2018 Kita-Tokarczyk .... C07C 219/06

FOREIGN PATENT DOCUMENTS

| CN | 105287289 | 3/2016 |
| EP | 0243145 | 7/1993 |
| EP | 22394653 | 12/2011 |
| EP | 2664327 | 11/2013 |
| JP | H09268115 | 10/1997 |
| WO | 2017097816 | 6/2017 |
| WO | WO-2017097816 A1 * | 6/2017 ............. A61K 8/345 |

OTHER PUBLICATIONS

Lopes (Pharmaceutics, 2014, vol. 6, pp. 52-77) (Year: 2014).*
International Search Report and Written Opinion in corresponding PCT/EP2018/081857, dated Feb. 20, 2019.
Office Action in co-pending U.S. Appl. No. 16/766,814, dated Jul. 20, 2021.
Office Action in co-pending U.S. Appl. No. 16/766,814, dated Oct. 5, 2021.
Lopes, "Overcoming the Cutaneous Barrier with Microemulsions", Pharm., 2014, 6, pp. 52-77.
Office Action in co-pending U.S. Appl. No. 16/766,822, dated Jun. 24, 2021.
International Search Report and Written Opinion in corresponding PCT/EP2018/081856, dated Dec. 21, 2018.
Azeem, et al., "Emerging Role of Microemulsions in Cosmetics", Recent Patents on Drug Delivery & Formulation, vol. 2, issue 3, Nov. 1, 2008, p. 275-289.

* cited by examiner

Primary Examiner — Mark V Stevens
(74) Attorney, Agent, or Firm — Hovey Williams LLP

(57) ABSTRACT

The present invention relates to a novel pharmaceutically active composition which is able to permeate into the deeper layers of the skin and the keratin sheets of nails. The composition is a microemulsion comprising at least an alcohol ethoxysulfate, an ethoxylated glyceryl fatty acid ester, and an ethoxylated sorbitol or sorbitol anhydride fatty acid ester. The composition may optionally comprise further additives like emollients, substances for hardening a nail, or substances for enhancing nail growth. The composition is particularly suitable for treating fungal infections of the skin or nails, such as athlete's foot and onychomycosis. The composition is also suitable for treating inflammatory skin diseases, such as psoriasis and atopic eczema.

19 Claims, No Drawings

COMPOSITION FOR TREATING ONYCHOMYCOSIS

RELATED APPLICATIONS

This application is the U.S. National Stage of International Patent Application No. PCT/EP2018/081857, filed Nov. 20, 2018, which is hereby incorporated by reference in its entirety, and which claims priority to European Patent Application No. 17204960.3, filed Dec. 1, 2017.

The present invention relates to a novel pharmaceutically active composition which is able to permeate into the deeper layers of the skin and the keratin sheets of nails. The composition is a microemulsion comprising at least an alcohol ethoxysulfate, an ethoxylated glyceryl fatty acid ester, and an ethoxylated sorbitol or sorbitol anhydride fatty acid ester. The composition may optionally comprise further additives like emollients, substances for hardening a nail, or substances for enhancing nail growth. The composition is particularly suitable for treating fungal infections of the skin or nails, such as athlete's foot and onychomycosis. The composition is also suitable for treating inflammatory skin diseases, such as psoriasis and atopic eczema.

BACKGROUND

Fungal skin infections are probably the most common skin diseases that affect millions of people worldwide. More than 90% of those infections are caused by dermatophytes, a group of fungi that are able to obtain the nutrients required for growth from keratinized material of the skin and nails. The symptoms of fungal skin infections like athlete's foot include skin lesions, itching and scaling. Fungal skin infections are often recurrent which makes treatment challenging.

Dermatophytes like *Trichophyton rubrum* and *Trichophyton mentagrophytes* are also the causative agent for onychomycosis, an infection of toe or finger nails that severely affects the quality of life. Since the disease is associated with significant impairments, such as pain and disfigurement, it constitutes an important public health problem. The infection can involve all parts of the nail, including the nail matrix, the nail bed, and the nail plate. Onychomycosis results in a significant change of the nail which often becomes thickened and discolored. In the course of the infection, onycholysis and nail plate dystrophy may occur.

A number of different treatments are known in the prior art for treating fungal skin and nail infections. Diseases like athlete's foot are often locally treated with creams that comprise antifungal agents such as clotrimazole, terbinafine or the like. However, since dermatophytes often infect areas of the skin which are difficult to access, treatment success is often limited. With onychomycosis, the problems associated with local treatment mainly reside in the inability of antifungal drugs to penetrate the nail plate in order to reach the infection sites beneath the nail. Therefore, onychomycosis is often treated systemically by orally administering antifungal agents like terbinafine or itraconazole. Systemic treatments however are clearly undesirable due to potential side effects of the antifungal drugs.

Accordingly, there is a need for novel non-systemic treatment concepts that are effective in treating fungal infections of the skin or nail which are free of side effects and associated with low costs. The present invention provides novel pharmaceutically active compositions which meet these demands.

DETAILED DESCRIPTION OF THE INVENTION

The present invention provides a novel pharmaceutically active composition which is able to effectively permeate into the keratin sheets of nails, thereby reaching all sites of infection and prevent the growth and propagation of the pathogenic fungi. It has been found in the course of the invention that by using three different types of surfactants, microemulsions can be formed that show particularly good skin and nail penetration properties. The microemulsions are capable of penetrating into the nail where they provide for an acidic environment that prevents the growth and metabolisms of the pathogenic fungi, e.g. the dermatophytes.

The pharmaceutically active composition of the invention is a microemulsion comprising the following components:
(a) an alcohol ethoxysulfate;
(b) an ethoxylated glyceryl fatty acid ester;
(c) an ethoxylated sorbitol or sorbitol anhydride fatty acid ester.

The pharmaceutically active composition of the invention comprises at least the three surfactants in amounts that allow the formation of a microemulsion. As used herein, a microemulsion refers to a macroscopically homogeneous mixture of water, oil and one or more surfactants. In the compositions of the present invention, one of the three surfactants can represent the oil component. Preferably, the PEG fatty acid ester may form the oil component of the composition.

As a first component, the composition of the invention comprises an alcohol ethoxysulfate (AES). Alcohol ethoxysulfates are a class of surfactants that is widely used in cosmetic and cleaning products. As used herein, the alcohol ethoxysulfate for use in the composition of the invention has the general formula (I) $R'-O-(CH_2-CH_2O)_n-SO_3M$ in which R' is an alkyl group or an alkylaryl group, n represents the average number of oxyethylene groups per molecule, and M is a cation.

In a preferred embodiment, the alcohol ethoxysulfate has the above formula (I) in which R' is a straight or branched alkyl group with 8-18 carbon atoms, or an alkylaryl group having an alkyl moiety having from 8 to 12 carbon atoms, n represents the average number of oxyethylene groups per molecule which is from 1 to 12, and M is a cation selected from an alkali metal ion, such as Na+ or Ka+, an ammonium ion, and mixtures thereof.

In another preferred embodiment, the alcohol ethoxysulfate has the above formula (I) in which R' is a straight or branched alkyl group with 8-18 carbon atoms, n represents the average number of oxyethylene groups per molecule which is from 1 to 8, and M is a cation selected from an alkali metal ion, such as Na+ or Ka+, an ammonium ion, and mixtures thereof.

In yet another preferred embodiment, the alcohol ethoxysulfate has the above formula (I) in which R' is a straight or branched alkyl group with 10-14 carbon atoms, n represents the average number of oxyethylene groups per molecule which is from 1 to 4, and M is a cation selected from an alkali metal ion, such as Na+ or Ka+, an ammonium ion, and mixtures thereof.

In yet another preferred embodiment, the alcohol ethoxysulfate has the above formula (I) in which R' is a straight alkyl group with 10-14 carbon atoms, n represents the average number of oxyethylene groups per molecule which is from 2 to 3, and M is a cation selected from an alkali metal ion.

In a particularly preferred embodiment, the alcohol ethoxysulfate has the above formula (I) in which R' is a straight alkyl group with 10-12 carbon atoms, n represents the average number of oxyethylene groups per molecule which is from 2 to 3, and M is a cation selected from Na+ or Ka+.

The alcohol ethoxysulfate is preferably a dodecyl alcohol ethoxysulfate. In a particularly preferred embodiment, the alcohol ethoxysulfate in the composition of the invention is sodium lauryl ether sulfate.

The alcohol ethoxysulfate is preferably present in the composition in an amount of 0.5 to 25.0% (w/w). This means that the alcohol ethoxysulfate can be present in an amount ranging from about 1.0 to about 20.0% (w/w), from about 1.0 to about 15.0% (w/w), from about 1.0 to about 10.0% (w/w), from about 1.0 to about 5.0% (w/w), from about 2.0 to about 25.0% (w/w), from about 2.0 to about 20.0% (w/w), from about 2.0 to about 15.0% (w/w), from about 2.0 to about 10.0% (w/w), from about 2.0 to about 5.0% (w/w), from about 3.0 to about 25.0% (w/w), from about 3.0 to about 20.0% (w/w), from about 3.0 to about 15.0% (w/w), from about 3.0 to about 10.0% (w/w), from about 3.0 to about 5.0% (w/w), from about 4.0 to about 25.0% (w/w), from about 4.0 to about 20.0% (w/w), from about 4.0 to about 15.0% (w/w), from about 4.0 to about 10.0% (w/w), or from about 4.0 to about 5.0% (w/w).

As used herein, the term "about", when used in combination with a numeric value shall mean±10% of said recited value.

In a particularly preferred embodiment, the alcohol ethoxysulfate is present in the composition in an amount of about 4.5 to about 5.5%, such as about 5% (w/w). In a particularly preferred embodiment, the composition of the invention comprises sodium lauryl ether sulfate in an amount of about 4.5 to about 5.5% (w/w), more preferably about 5% (w/w).

As a second component, the composition of the present invention comprises an ethoxylated glyceryl fatty acid ester. Ethoxylated glyceryl fatty acid esters are esters of glycerol with one or more fatty acids to which polyethylene glycol has been added. While the hydrophilic polyethylene glycol part of the molecule is hydrophilic, the fatty acid residue is lipophilic. Owing to their amphiphilic properties, ethoxylated glyceryl fatty acid esters are commonly used as surfactants in cosmetic products.

The number of ethylene glycol groups in the molecule is not particularly relevant. The ethoxylated glyceryl esters for use in the present invention may comprise about 1-600 repeating ethylene glycol groups, such as about 1-500, about 1-400, about 1-300, about 1-200, about 1-100, about 1-90, about 1-80, about 1-70, about 1-60, about 1-50, about 1-40, about 1-30, about 1-20, about 1-10, or about 1-5. An ethoxylated glyceryl ester with 1-10 ethylene glycol groups is particularly preferred. In a preferred embodiment, the ethoxylated glyceryl ester comprises 7 ethylene glycol groups.

The ethoxylated glyceryl ester can be a mono-, di-, or triester, or a mixture of those. In a preferred embodiment, the ester is a monoester. The ethoxylated glyceryl ester may be an ester of glycerol with saturated or unsaturated fatty acids. Suitable saturated fatty acids include caprylic acid (C8), capric acid (C10), lauric acid (C12), myristic acid (C14), palmitic acid (C16), stearic acid (C18), arachidic acid (C20), behenic acid (C22), lignoceric acid (C24) and cerotic acid (C26). Suitable unsaturated fatty acids include myristoleic acid (C14), palmitoleic acid (C16), sapienic acid (C16), oleic acid (C18), elaidic acid (C18), vaccenic acid (C18), linoleic acid (C18), arachidonic acid (C20), eisopentaenoic acid (C20), erucic acid (C22), and docohexaenoic acid (C22).

In one preferred embodiment, the ethoxylated glyceryl ester is an ethoxylated glyceryl cocoate, i.e. an ester of glycerol with coconut-oil derived fatty acids. In another preferred embodiment, the ethoxylated glyceryl ester is an ethoxylated glyceryl cocoate monoester. Preferably, the ethoxylated glyceryl cocoate contains about 1-80, about 1-40, about 1-20, about 1-10 or 1-7 repeating ethylene glycol groups. Examples for suitable cocoate esters include, but are not limited to, PEG-7 glyceryl cocoate, PEG-30 glyceryl cocoate, PEG-40 glyceryl cocoate, PEG-78 glyceryl cocoate and PEG-80 glyceryl cocoate. In a particularly preferred embodiment, the ethoxylated glyceryl cocoate is PEG-7 glyceryl cocoate, which is commercially available, for instance, as Cetiol HE (BASF, Ludwigshafen, Germany).

The ethoxylated glyceryl fatty acid ester is preferably present in the composition in an amount of 1.0 to 50.0% (w/w). This means that the ethoxylated glyceryl fatty acid ester can be present in a range from about 1.0 to about 45.0% (w/w), from about 1.0 to about 40.0% (w/w), from about 1.0 to about 35.0% (w/w), from about 1.0 to about 30.0% (w/w), from about 1.0 to about 25.0% (w/w), from about 1.0 to about 20.0% (w/w), from about 1.0 to about 15.0% (w/w), from about 1.0 to about 10.0% (w/w), from about 5.0 to about 45.0% (w/w), about from 5.0 to about 40.0% (w/w), from about 5.0 to about 35.0% (w/w), from about 5.0 to about 30.0% (w/w), from about 5.0 to about 25.0% (w/w), from about 5.0 to about 20.0% (w/w), from about 5.0 to about 15.0% (w/w), from about 5.0 to about 10.0% (w/w), from about 7.5 to about 45.0% (w/w), from about 7.5 to about 40.0% (w/w), from about 7.5 to about 35.0% (w/w), from about 7.5 to about 30.0% (w/w), from about 7.5 to about 25.0% (w/w), from about 7.5 to about 20.0% (w/w), from about 7.5 to about 15.0% (w/w), or from about 7.5 to about 10.0% (w/w). In a preferred embodiment, the ethoxylated glyceryl fatty acid ester is present in the composition in an amount of about 7.5 to about 15.0%, such as about 10% (w/w).

In a preferred embodiment, the ethoxylated glyceryl fatty acid ester is present in the composition in an amount of about 9.5 to about 10.5%, such as about 10.0% (w/w). In an even more preferred embodiment, the composition of the invention comprises an ethoxylated glyceryl cocoate in an amount of about 9.5 to about 10.5% (w/w), more preferably about 10.0% (w/w). In a most preferred embodiment, the composition of the invention comprises PEG-7 glyceryl cocoate in an amount of about 9.5 to about 10.5% (w/w), more preferably about 10.0% (w/w).

As a third component, the composition of the invention comprises an ethoxylated sorbitol or sorbitol anhydride fatty acid ester. These esters are based on the polyhydric sugar alcohol sorbitol or its anhydrides, e.g. sorbitan. Preferably, the ethoxylated sorbitol or sorbitol anhydride fatty acid ester is a partial ester which means that part of the hydroxyl groups in the sorbitol or sorbitol anhydride are not esterified. The sorbitol or sorbitol anhydride ester may be an ester with any type of saturated or unsaturated fatty acids.

Suitable saturated fatty acids include caprylic acid (C8), capric acid (C10), lauric acid (C12), myristic acid (C14), palmitic acid (C16), stearic acid (C18), arachidic acid (C20), behenic acid (C22), lignoceric acid (C24) and cerotic acid (C26). Suitable unsaturated fatty acids include myristoleic acid (C14), palmitoleic acid (C16), sapienic acid (C16), oleic acid (C18), elaidic acid (C18), vaccenic acid (C18), linoleic acid (C18), arachidonic acid (C20), eisopentaenoic acid (C20), erucic acid (C22), and doco-hexaenoic acid (C22).

In a preferred embodiment, the ethoxylated sorbitol or sorbitol anhydride fatty acid ester is an oleic acid, stearic acid, or lauric acid ester. A partial ester of sorbitol with oleic acid, stearic acid, or lauric acid is most preferred. The composition may comprise a mixture of different esters or partial esters of sorbitol or sorbitol anhydride with different fatty acids, such as a mixture of different partial esters of sorbitol or a sorbitol anhydride with oleic acid, stearic acid, or lauric acid.

Preferably, the ethoxylated sorbitol or sorbitol anhydride ester contains about 1-85, about 1-40, about 1-20, about 1-10 or about 1-5 ethylene glycol groups.

It is particularly preferred that the ethoxylated sorbitol or sorbitol anhydride ester is selected from the group consisting of polysorbate 20, polysorbate 21, polysorbate 40, polysorbate 60, polysorbate 61, polysorbate 65, polysorbate 80, polysorbate 81, polysorbate 85, and polysorbate 120. Polysorbate 80 is particularly preferred.

The ethoxylated sorbitol or sorbitol anhydride ester is preferably present in the composition in an amount of about 0.5 to about 25.0% (w/w). This means that the ethoxylated sorbitol or sorbitol anhydride ester can be present in a range from about 1.0 to about 20.0% (w/w), from about 1.0 to about 15.0% (w/w), from about 1.0 to about 10.0% (w/w), from about 1.0 to about 8.0% (w/w), from about 2.0 to about 25.0% (w/w), from about 2.0 to about 20.0% (w/w), from about 2.0 to about 15.0% (w/w), from about 2.0 to about 10.0% (w/w), from about 2.0 to about 8.0% (w/w), from about 3.0 to about 25.0% (w/w), from about 3.0 to about 20.0% (w/w), from about 3.0 to about 15.0% (w/w), from about 3.0 to about 10.0% (w/w), from about 3.0 to about 8.0% (w/w), from about 4.0 to about 25.0% (w/w), from about 4.0 to about 20.0% (w/w), from about 4.0 to about 15.0% (w/w), from about 4.0 to about 10.0% (w/w), or from about 4.0 to about 8.0% (w/w). In a most preferred embodiment, the ethoxylated sorbitol or sorbitol anhydride ester is preferably present in the composition in an amount of about 6.0 to about 9.0%, such as about 8.0% (w/w).

In a preferred embodiment, the composition of the invention comprises an ethoxylated sorbitol ester in an amount of about 6.0 to about 9.0%, such as about 8.0% (w/w). In an even more preferred embodiment, the composition comprises a polysorbate in an amount of about 9.5 to about 10.5% (w/w), more preferably about 10.0% (w/w). In a most preferred embodiment, the composition of the invention comprises polysorbate 80 in an amount of about 9.5 to about 10.5% (w/w), more preferably about 10.0% (w/w).

It is preferred that the weight ratio of ethoxylated glyceryl fatty acid ester/alcohol ethoxysulfate/ethoxylated sorbitol or sorbitol anhydride fatty acid ester is approximately 3:2:1, more preferably 2.5:1.8:1 and even more preferably 2:1.6:1.

In a preferred embodiment, the pharmaceutically active composition of the invention is a microemulsion comprising the following components:
(a) an alcohol ethoxysulfate in an amount of about 0.5 to about 25.0% (w/w),
(b) an ethoxylated glyceryl fatty acid ester in an amount of about 1.0 to about 50.0% (w/w), and
(c) an ethoxylated sorbitol or sorbitol anhydride fatty acid ester in an amount of about 0.5 to about 25.0% (w/w).

In another preferred embodiment, the pharmaceutically active composition of the invention is a microemulsion comprising the following components:
(a) an alcohol ethoxysulfate in an amount of about 0.5 to about 10.0% (w/w),
(b) an ethoxylated glyceryl fatty acid ester in an amount of about 1.0 to about 20.0% (w/w), and
(c) an ethoxylated sorbitol or sorbitol anhydride fatty acid ester in an amount of about 0.5 to about 15.0% (w/w).

In another preferred embodiment, the pharmaceutically active composition of the invention is a microemulsion comprising the following components:
(a) an alcohol ethoxysulfate in an amount of about 0.5 to about 5.0% (w/w),
(b) an ethoxylated glyceryl fatty acid ester in an amount of about 1.0 to about 10.0% (w/w), and
(c) an ethoxylated sorbitol or sorbitol anhydride fatty acid ester in an amount of about 0.5 to about 8.0% (w/w).

In yet another preferred embodiment, the pharmaceutically active composition of the invention is a microemulsion comprising the following components:
(a) an alcohol ethoxysulfate,
(b) an ethoxylated glyceryl cocoate, and
(c) a polysorbate.

In yet another preferred embodiment, the pharmaceutically active composition of the invention is a microemulsion comprising the following components:
(a) sodium lauryl ether sulfate,
(b) PEG-7 glyceryl cocoate, and
(c) polysorbate 80.

In yet another preferred embodiment, the pharmaceutically active composition of the invention is a microemulsion comprising the following components:
(a) an alcohol ethoxysulfate in an amount of about 0.5 to about 25.0% (w/w),
(b) an ethoxylated glyceryl cocoate in an amount of about 1.0 to about 50.0% (w/w), and
(c) a polysorbate in an amount of about 0.5 to about 25.0% (w/w).

In yet another preferred embodiment, the pharmaceutically active composition of the invention is a microemulsion comprising the following components:
(a) sodium lauryl ether sulfate in an amount of about 0.5 to about 25.0% (w/w),
(b) PEG-7 glyceryl cocoate in an amount of about 1.0 to about 50.0% (w/w), and
(c) polysorbate 80 in an amount of about 0.5 to about 25.0% (w/w).

In yet another preferred embodiment, the pharmaceutically active composition of the invention is a microemulsion comprising the following components:
(a) sodium lauryl ether sulfate in an amount of about 0.5 to about 10.0% (w/w),
(b) an ethoxylated glyceryl cocoate in an amount of about 1.0 to about 20.0% (w/w), and
(c) a polysorbate in an amount of about 0.5 to about 15.0% (w/w).

In yet another preferred embodiment, the pharmaceutically active composition of the invention is a microemulsion comprising the following components:
(a) sodium lauryl ether sulfate in an amount of about 0.5 to about 10.0% (w/w),
(b) PEG-7 glyceryl cocoate in an amount of about 1.0 to about 20.0% (w/w), and
(c) polysorbate 80 in an amount of about 0.5 to about 15.0% (w/w).

In yet another preferred embodiment, the pharmaceutically active composition of the invention is a microemulsion comprising the following components:
(a) sodium lauryl ether sulfate in an amount of about 0.5 to about 5.0% (w/w),
(b) an ethoxylated glyceryl cocoate in an amount of about 1.0 to about 10.0% (w/w), and (c) a polysorbate in an amount of about 0.5 to about 8.0% (w/w).

In yet another preferred embodiment, the pharmaceutically active composition of the invention is a microemulsion comprising the following components:
(a) sodium lauryl ether sulfate in an amount of 5.0% (w/w),
(b) PEG-7 glyceryl cocoate in an amount of about 10.0% (w/w), and
(c) polysorbate 80 in an amount of about 8.0% (w/w).

Apart from the surfactants, the compositions of the invention typically comprise further components. These components depend on the intended use of the composition. In one embodiment, the pharmaceutical composition as defined above is formulated for use in a method of treating a fungal infection of the skin or nails. Fungi, and in particular dermatophytes which are the common cause of fungal skin and nail infections, require a basic pH environment. At acidic pH, the metabolic activities of dermatophytes cease and the organisms eventually die. For this reason, a composition for treating a fungal infection of the skin or nails should have an acidic pH. The composition may have a pH in the range from about 2.5 to about 6.5, preferably from about 2.5 to about 5.5, and more preferably from about 3.0 to about 5.0 or from about 3.0 to about 4.0. The acidic pH can be achieved by adding an acid to the microemulsion, e.g. a carboxylic acid, such as an alpha hydroxy acid. For application to the human skin or nail, lactic acid is particularly useful, as it is also secreted by the skin flora to form the protective acidic milieu on the human skin surface.

The nature of the carboxylic acid that can be used in the composition of the invention is not limited. Suitable carboxylic acids include formic acid, acetic acid, propionic acid, butyric acid, valeric acid, caproic acid, enanthic acid, caprylic acid, and the like. The carboxylic acid that is used for adjusting the composition to an acidic pH can be present in the composition in an amount of 0.01 (w/w) to 3.0 (w/w), preferably 0.05% (w/w) to 2.0% (w/w), 0.1% (w/w) to 1.0% (w/w), such as 0.01 (w/w), 0.02 (w/w), 0.03 (w/w), 0.04 (w/w), 0.05% (w/w), 0.06% (w/w), 0.07% (w/w), 0.08% (w/w), 0.09% (w/w), 0.1% (w/w), 0.1% (w/w), 0.11% (w/w), 0.12% (w/w), 0.13% (w/w), 0.14% (w/w), or 0.15% (w/w). It is particularly preferred that the carboxylic acid is present in the composition in an amount of 0.1% (w/w). It is also particularly preferred that the carboxylic acid that is present in the composition is lactic acid.

A pharmaceutical composition intended for treating nail infections may further comprise biotin as an optional additive. It is well known that biotin enhances the growth of hairs and nails. For nails infected with dermatophytes, it is often required to continue treatment for several months until the infected sites have completely outgrown and replaced by healthy nail. To expedite this process, biotin may be added to the composition of the invention. Preferably, the biotin is present in the composition of the invention in an amount of 0.0001 to 0.05% (w/w), preferably 0.001 to 0.01% (w/w). An amount of 0.0005% (w/w) has been found to be particularly suitable for nail treatments.

Since dermatophytes damage the structure of the nail, it may be further desired to add a compound to a composition intended for treating nail infections which effectively hardens the nail. For example, a composition for nail treatment may include calcium chloride for this purpose. The calcium chloride is preferably present in the composition in an amount of about 0.1 to about 10.0% (w/w), e.g. about 0.5 to about 8.0% (w/w), about 0.6 to about 8.0% (w/w), about 0.7 to about 6.0% (w/w), about 0.8 to about 5.0% (w/w), about 0.9 to about 3.0% (w/w), or about 1.0 to about 2.0% (w/w), such as about 1.0 or about 1.5% (w/w), Another useful component in a pharmaceutical composition for treating nail infections is a compound that is able to soften the keratin in the nail, such as urea. By softening the keratin structures in the nail, urea assists in the permeation of the pharmaceutical composition into deeper layers of the nail structure. Urea is preferably present in the composition in an amount of about 0.5 to about 25.0% (w/w). This means that urea can be present in a range from about 1.0 to about 20.0% (w/w), from about 1.0 to about 15.0% (w/w), from about 1.0 to about 10.0% (w/w), from about 2.0 to about 25.0% (w/w), from about 2.0 to about 20.0% (w/w), from about 2.0 to about 15.0% (w/w), from about 2.0 to about 10.0% from about 3.0 to about 25.0% (w/w), from about 3.0 to about 20.0% (w/w), from about 3.0 to about 15.0% (w/w), from about 3.0 to about 10.0% (w/w), from about 4.0 to about 25.0% (w/w), from about 4.0 to about 20.0% (w/w), from about 4.0 to about 15.0% (w/w), from about 4.0 to about 10.0% (w/w). In a most preferred embodiment, urea is present in the composition in an amount of about 4.0 to about 6.0%, such as about 5.0% (w/w).

Hence, in a preferred embodiment, the composition of the invention is formulated as a microemulsion for treating a fungal infection of the nails and comprises:
(a) an alcohol ethoxysulfate in an amount of about 0.5 to about 25.0% (w/w),
(b) an ethoxylated glyceryl cocoate in an amount of about 1.0 to about 50.0% (w/w), and
(c) a polysorbate in an amount of about 0.5 to about 25.0% (w/w),
said microemulsion having a pH from 2.5 to 6.5, preferably from 2.5 to 5.5, and more preferably from 3.0 to 5.0 or from 3.0 to 4.0.

In yet another preferred embodiment, the composition of the invention is formulated as a microemulsion for treating a fungal infection of the nails and comprises:
(a) sodium lauryl ether sulfate in an amount of about 0.5 to about 25.0% (w/w),
(b) PEG-7 glyceryl cocoate in an amount of about 1.0 to about 50.0% (w/w), and
(c) polysorbate 80 in an amount of about 0.5 to about 25.0% (w/w),
said microemulsion having a pH from 3.0 to 5.0, preferably from 3.0 to 4.0.

In yet another preferred embodiment, the composition of the invention is formulated as a microemulsion for treating a fungal infection of the nails and comprises:
(a) sodium lauryl ether sulfate in an amount of about 0.5 to about 10.0% (w/w),
(b) an ethoxylated glyceryl cocoate in an amount of about 1.0 to about 20.0% (w/w), and
(c) a polysorbate in an amount of about 0.5 to about 15.0% (w/w),
said microemulsion having a pH from 3.0 to 4.0.

In yet another preferred embodiment, the composition of the invention is formulated as a microemulsion for treating a fungal infection of the nails and comprises:
(a) sodium lauryl ether sulfate in an amount of about 0.5 to about 10.0% (w/w),
(b) PEG-7 glyceryl cocoate in an amount of about 1.0 to about 20.0% (w/w), and
(c) polysorbate 80 in an amount of about 0.5 to about 15.0% (w/w),
said microemulsion having a pH from 2.5 to 6.5, preferably from 2.5 to 5.5, and more preferably from 3.0 to 5.0 or from 3.0 to 4.0.

In yet another preferred embodiment, the composition of the invention is formulated as a microemulsion for treating a fungal infection of the nails and comprises:
(a) sodium lauryl ether sulfate in an amount of about 0.5 to about 5.0% (w/w),
(b) an ethoxylated glyceryl cocoate in an amount of about 1.0 to about 10.0% (w/w), and
(c) a polysorbate in an amount of about 0.5 to about 8.0% (w/w),
said microemulsion having a pH from 3.0 to 5.0, preferably from 3.0 to 4.0.

In yet another preferred embodiment, the composition of the invention is formulated as a microemulsion for treating a fungal infection of the nails and comprises:
(a) sodium lauryl ether sulfate in an amount of 5.0% (w/w),
(b) PEG-7 glyceryl cocoate in an amount of about 10.0% (w/w), and
(c) polysorbate 80 in an amount of about 8.0% (w/w),
said microemulsion having a pH from 3.0 to 4.0.

The addition of urea to a composition for treating nail infections is particularly preferred according to the invention for softening the keratin structures in the nail. Thus, in a preferred embodiment, the composition of the invention is formulated as a microemulsion for treating a fungal infection of the nails and comprises:
(a) an alcohol ethoxysulfate in an amount of about 0.5 to about 25.0% (w/w),
(b) an ethoxylated glyceryl cocoate in an amount of about 1.0 to about 50.0% (w/w),
(c) a polysorbate in an amount of about 0.5 to about 25.0% (w/w), and
(d) urea in an amount of about 0.5 to about 25.0%,
said microemulsion having a pH from 2.5 to 6.5, preferably from 2.5 to 5.5, and more preferably from 3.0 to 5.0 or from 3.0 to 4.0.

In yet another preferred embodiment, the composition of the invention is formulated as a microemulsion for treating a fungal infection of the nails and comprises:
(a) sodium lauryl ether sulfate in an amount of about 0.5 to about 25.0% (w/w),
(b) PEG-7 glyceryl cocoate in an amount of about 1.0 to about 50.0% (w/w),
(c) polysorbate 80 in an amount of about 0.5 to about 25.0% (w/w), and
(d) urea in an amount of about 0.5 to about 25.0%,
said microemulsion having a pH from 3.0 to 5.0, preferably from 3.0 to 4.0.

In yet another preferred embodiment, the composition of the invention is formulated as a microemulsion for treating a fungal infection of the nails and comprises:
(a) sodium lauryl ether sulfate in an amount of about 0.5 to about 10.0% (w/w),
(b) an ethoxylated glyceryl cocoate in an amount of about 1.0 to about 20.0% (w/w), and
(c) a polysorbate in an amount of about 0.5 to about 15.0% (w/w), and
(d) urea in an amount of about 0.5 to about 10.0%,
said microemulsion having a pH from 3.0 to 4.0.

In yet another preferred embodiment, the composition of the invention is formulated as a microemulsion for treating a fungal infection of the nails and comprises:
(a) sodium lauryl ether sulfate in an amount of about 0.5 to about 10.0% (w/w),
(b) PEG-7 glyceryl cocoate in an amount of about 1.0 to about 20.0% (w/w),
(c) polysorbate 80 in an amount of about 0.5 to about 15.0% (w/w), and
(d) urea in an amount of about 0.5 to about 25.0%,
said microemulsion having a pH from 2.5 to 6.5, preferably from 2.5 to 5.5, and more preferably from 3.0 to 5.0 or from 3.0 to 4.0.

In yet another preferred embodiment, the composition of the invention is formulated as a microemulsion for treating a fungal infection of the nails and comprises:
(a) sodium lauryl ether sulfate in an amount of about 0.5 to about 5.0% (w/w),
(b) an ethoxylated glyceryl cocoate in an amount of about 1.0 to about 10.0% (w/w), and
(c) a polysorbate in an amount of about 0.5 to about 8.0% (w/w), and
(d) urea in an amount of about 0.5 to about 5.0%,
said microemulsion having a pH from 3.0 to 5.0, preferably from 3.0 to 4.0.

In yet another preferred embodiment, the composition of the invention is formulated as a microemulsion for treating a fungal infection of the nails and comprises:
(a) sodium lauryl ether sulfate in an amount of 5.0% (w/w),
(b) PEG-7 glyceryl cocoate in an amount of about 10.0% (w/w),
(c) polysorbate 80 in an amount of about 8.0% (w/w), and
(d) urea in an amount of about 5.0%,
said microemulsion having a pH from 3.0 to 4.0.

A pharmaceutical composition as described above is suitable for being used in the treatment of a fungal infection of the nails, preferably human nails. By continuously applying the composition to an infected nail, the microemulsion penetrates into the nail and creates an acidic environment which effectively kills dermatophytes and other pathogenic fungi. Accordingly, the pharmaceutical composition is particularly suitable for treating onychomycosis, such as onychomycosis of the finger or toe nail. The treatment comprises the application of the microemulsion directly onto the infected nail, preferably once or twice daily. The treatment is preferably continued for a period of at least two months, at least three months, at least four months, at least five months, at least six months, at least eight months, or at least twelve months. It is particularly preferred that the treatment is continued until the infected nail has been completely replaced with healthy nail. Compositions that are to be administered to the nail can be packaged into dropping bottles that allow the dripping of the microemulsion directly onto the nail. Alternatively, the microemulsion can be formulated as a nail varnish that is applied with a small brush.

In a preferred embodiment, a composition for the treatment of a fungal infection of the nails as described above can comprise additional active ingredients that are known to be effective against fungi, and in particular dermatophytes. Due to the acidic pH of the compositions of the invention that are formulated for treating fungal infections, the additional active ingredients should be stable in an acidic environment. Suitable active ingredients include terbinafine, miconazole, and ciclopirox, all of which are stable at a ph of about 3, as well as bifonazole and clotrimazole, which are stable at a ph of about 5. Typically, terbinafine can be added to the composition in an amount of about 0.1 to about 2.0% (w/w), preferably about 0.5 to about 1.5% (w/w), and more preferably about 1.0% (w/w). Miconazole can be added to the composition in an amount of about 0.5 to about 5.0% (w/w), preferably about 2.0 to about 3.0% (w/w), and more preferably about 2.5% (w/w). Ciclopirox can be added to the composition in an amount of about 1.0 to about 10.0% (w/w), preferably about 2.0 to about 7.5% (w/w), and more preferably about 5.0% (w/w). Bifonazole can be added to the composition in an amount of about 0.1 to about 1.5% (w/w), preferably about 0.5 to about 1.0% (w/w), and more preferably about 0.75% (w/w). Finally, clotrimazole can be added to the composition in an amount of about 0.1 to about 1.5% (w/w), preferably about 0.5 to about 1.0% (w/w), and more preferably about 0.75% (w/w).

In another preferred embodiment, a composition for the treatment of a fungal infection of the nails as described above does not comprise any additional active ingredients that are known to be effective against fungi. In other words, the fungicidal effect of the composition is effected solely by the reduction of the pH in the infected nail.

The compositions of the present invention can also be used for treating fungal skin infections. In that case, the microemulsion is directly applied to the infected skin sites. With respect to the surfactant components, the composition intended for fungal skin infections are composed as the compositions referred to above in the context with nail treatment. This means that the type of surfactants and the amounts used in the final compositions are the same as described above for the compositions intended for nail treatment. However, the compositions for treating fungal skin infections may differ in the type of additives. For example, a composition for treating fungal skin infections may include additives for improving hydration of the skin, like dexpanthenol.

Thus, in a preferred embodiment the composition of the invention is formulated as a microemulsion for treating a fungal infection of the skin and comprises:
(a) an alcohol ethoxysulfate in an amount of about 0.5 to about 25.0% (w/w),
(b) an ethoxylated glyceryl cocoate in an amount of about 1.0 to about 50.0% (w/w),
(c) a polysorbate in an amount of about 0.5 to about 25.0% (w/w),
(d) urea in an amount of about 0.5 to about 25.0%, and
(e) optionally, dexpanthenol in an amount of about 0.5 to about 10.0%,
said microemulsion having a pH from 2.5 to 6.5, preferably from 2.5 to 5.5, and more preferably from 3.0 to 5.0 or from 3.0 to 4.0.

In yet another preferred embodiment, the composition of the invention is formulated as a microemulsion for treating a fungal infection of the skin and comprises:
(a) sodium lauryl ether sulfate in an amount of about 0.5 to about 25.0% (w/w),
(b) PEG-7 glyceryl cocoate in an amount of about 1.0 to about 50.0% (w/w),
(c) polysorbate 80 in an amount of about 0.5 to about 25.0% (w/w),
(d) urea in an amount of about 0.5 to about 25.0%, and
(e) optionally, dexpanthenol in an amount of about 0.5 to about 10.0%,
said microemulsion having a pH from 3.0 to 5.0, preferably from 3.0 to 4.0.

In yet another preferred embodiment, the composition of the invention is formulated as a microemulsion for treating a fungal infection of the skin and comprises:
(a) sodium lauryl ether sulfate in an amount of about 0.5 to about 10.0% (w/w),
(b) an ethoxylated glyceryl cocoate in an amount of about 1.0 to about 20.0% (w/w), and
(c) a polysorbate in an amount of about 0.5 to about 15.0% (w/w),
(d) urea in an amount of about 0.5 to about 10.0%, and
(e) optionally, dexpanthenol in an amount of about 0.5 to about 10.0%,
said microemulsion having a pH from 3.0 to 4.0.

In yet another preferred embodiment, the composition of the invention is formulated as a microemulsion for treating a fungal infection of the skin and comprises:
(a) sodium lauryl ether sulfate in an amount of about 0.5 to about 10.0% (w/w),
(b) PEG-7 glyceryl cocoate in an amount of about 1.0 to about 20.0% (w/w),
(c) polysorbate 80 in an amount of about 0.5 to about 15.0% (w/w),
(d) urea in an amount of about 0.5 to about 25.0%, and
(e) optionally, dexpanthenol in an amount of about 0.5 to about 10.0%,
said microemulsion having a pH from 2.5 to 6.5, preferably from 2.5 to 5.5, and more preferably from 3.0 to 5.0 or from 3.0 to 4.0.

In yet another preferred embodiment, the composition of the invention is formulated as a microemulsion for treating a fungal infection of the skin and comprises:
(a) sodium lauryl ether sulfate in an amount of about 0.5 to about 5.0% (w/w),
(b) an ethoxylated glyceryl cocoate in an amount of about 1.0 to about 10.0% (w/w), and
(c) a polysorbate in an amount of about 0.5 to about 8.0% (w/w),
(d) urea in an amount of about 0.5 to about 10.0%, and
(e) optionally, dexpanthenol in an amount of about 0.5 to about 10.0%,
said microemulsion having a pH from 3.0 to 5.0, preferably from 3.0 to 4.0.

In yet another preferred embodiment, the composition of the invention is formulated as a microemulsion for treating a fungal infection of the skin and comprises:
(a) sodium lauryl ether sulfate in an amount of 5.0% (w/w),
(b) PEG-7 glyceryl cocoate in an amount of 10.0% (w/w),
(c) polysorbate 80 in an amount of 8.0% (w/w),
(d) urea in an amount of 10.0%, and
(e) dexpanthenol in an amount of 5.0%,
said microemulsion having a pH from 3.0 to 4.0.

Fungal skin infections that can be treated with the compositions of the invention include, amongst others, ringworm, *Tinea cruris*, *Tinea capitis* and *Tinea pedis*.

Compositions that are to be administered to the skin are normally formulated to allow their transdermal delivery. For this, the microemulsions for skin treatment can be directly administered topically to the skin area to be treated. For example, the microemulsions referred to above can be packaged into dropping bottles that allow the dripping of the microemulsion directly onto the skin area in need of treatment. Alternatively, the compositions can be packaged into pump dispensers which allow spraying the microemulsion onto the skin areas to be treated. The microemulsions may also be formulated into ointments, creams, suspensions, lotions, pastes, gels, hydrogels, sprays, foams or oils. The microemulsions can also be incorporated into patches.

The compositions described above in the context of fungal skin infections can also be used for treating or ameliorating the symptoms of inflammatory skin diseases. As used herein, inflammatory skin diseases comprise psoriasis, atopic eczema, rosacea, eczema, seborrhea, acne, skin hypersensitivity reactions, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia and vitiligo. The treatment of psoriasis and atopic eczema is particularly preferred.

EXAMPLES

The following examples describe certain preferred embodiments of the present invention. It is however to be noted that the invention is not limited to such embodiments.

Example 1: Composition for Treating Fungal Nail Infections

A composition for treating fungal nail infections, and in particular onychomycosis, was prepared as followed:

| 1. | Cetiol HE | 10.0 g |
| 2. | Polysorbat 80 | 8.0 g |
| 3. | Texapon NSO | 5.0 g |
| 4. | Urea | 5.0 g |
| 5. | Lactic acid | 0.7 g |
| 6. | Benzalkoniumchlorid (1:1) | 0.2 g |
| 7. | Aqua dem. | ad 100 g |

Components 1 to 3 were mixed by slowly stirring at room temperature to provide pre-mix A. At the same time, components 4 to 7 were mixed by stirring at room temperature to provide pre-mix B. Pre-mix A and pre-mix B were mixed under slow stirring to result in a transparent microemulsion having a pH of 3.0. The microemulsion was filled into dropping bottles having a volume of 10 ml.

Example 2: Composition for Treating Fungal Nail Infections

A composition for treating fungal nail infections, and in particular onychomycosis, was prepared as followed:

| 1. | Cetiol HE | 10.0 g |
| 2. | Polysorbat 80 | 8.0 g |
| 3. | Texapon NSO | 5.0 g |
| 4. | CaCl$_2$ dihydrate | 1.0 g |
| 5. | Lactic acid | 0.1 g |
| 6. | Biotin | 0.005 g |
| 7. | Benzalkoniumchlorid (1:1) | 0.2 g |
| 8. | Aqua dem. | ad 100 g |

Components 1 to 3 were mixed by slowly stirring at room temperature to provide pre-mix A. At the same time, components 4 to 8 were mixed by stirring at a temperature of 70° C. to provide pre-mix B. Pre-mix A and pre-mix B were mixed under slow stirring to result in a transparent microemulsion having a pH of 4.0. The microemulsion was filled into dropping bottles having a volume of 10 ml.

Example 3: Composition for Treating Skin Dermatophytes

A composition for treating fungal skin infections was prepared as followed:

| 1. | Cetiol HE | 10.0 g |
| 2. | Polysorbat 80 | 8.0 g |
| 3. | Texapon NSO | 5.0 g |
| 4. | Urea | 10.0 g |
| 5. | Dexpanthenol | 5.0 g |
| 6. | Lactic acid | 1.0 g |
| 7. | Oleum salviae | 0.5 g |
| 8. | Benzalkoniumchlorid (1:1) | 0.2 g |
| 9. | Aqua dem. | ad 100 g |

Components 1 to 3 were mixed by slowly stirring at room temperature to provide pre-mix A. At the same time, components 4-6 and 8-9 were mixed by stirring at room temperature until they were completely dissolved to provide pre-mix B. Pre-mix A and pre-mix B were mixed under slow stirring to result in a transparent microemulsion having a pH of 3.2. In a final step, component 7 was added. The microemulsion was filled into spraying bottles having a volume of 100 ml.

Example 4: Composition for Treating Inflammatory Skin Diseases

A composition for treating inflammatory skin diseases was prepared as followed:

| 1. | Cetiol HE | 10.0 g |
| 2. | Polysorbat 80 | 8.0 g |
| 3. | Texapon NSO | 5.0 g |
| 4. | Urea | 10.0 g |
| 5. | Dexpanthenol | 5.0 g |
| 6. | Lactic acid | 0.2 g |
| 7. | Lauromacrogol | 2.0 g |
| 8. | Evening primrose oil | 1.0 g |
| 9. | Benzalkoniumchlorid (1:1) | 0.1 g |
| 10. | Aqua dem. | ad 100 g |

Components 1 to 3 were mixed by slowly stirring at room temperature. Evening primrose oil was added to provide pre-mix A. At the same time, components 4-7 and 8-10 were mixed by stirring at 40° C. until they were completely dissolved to provide pre-mix B. Pre-mix A and pre-mix B were mixed under slow stirring at room temperature to result in a transparent microemulsion. The microemulsion was filled into spraying bottles having a volume of 100 ml.

Example 5: Treatment of Onychomycosis—Study 1

The microemulsions of Examples 1 and 2 and the spray of Example 3 were tested in several experimental studies. In a first study, 30 patients at the age of 30-85 years that had been diagnosed with onychomycosis were treated either with (i) the microemulsion of Example 1 in combination with the spray of Example 3 or (ii) the microemulsions of Examples 1 and 2 in combination with the spray of Example 3. All patients had a history of one or more unsuccessful treatments, including systemic treatment with terbinafine, nail varnishes, tinctures and ointments.

The patients were assigned to two test groups of nearly the same average age. The patients of group A received the microemulsions of Examples 1 and 2 in combination with the spray of Example 3 for daily application. This group applied one drop of the microemulsion of Example 1 to the nail in the morning and one drop of the microemulsion of Example 2 in the evening. The spray of Example 3 was applied to the entire foot both in the morning and the evening.

The patients of group B received only the microemulsion of Example 1 in combination with the spray of Example 3 for daily application. This group applied one drop of the microemulsion of Example 1 to the nail in the morning and one drop in the evening. The spray of Example 3 was applied to the entire foot both in the morning and the evening.

All patients changed socks daily. Socks were washed at 60-65° C. The shoes of all patients were disinfected regularly. All patients were examined every 3-4 weeks.

Results: It was observed that all patients showed a clear improvement of the infected site after 3 months of treatment. Due to the addition of biotin in the microemulsion of Example 2, the patients of group A showed a faster nail growth and thus a faster healing. In addition, nails of patients from group A appeared slightly harder and healthier than those from group B. On Average, patients in group A showed a healing 2-3 months faster compared to group B. Within group A patients with an age up to 55 showed complete healing within 10 months. Patients older than 55 showed delayed healing within 13-14 months. After 18 months, all patients from both groups no longer showed any signs of onychomycosis.

Example 6: Treatment of Onychomycosis—Study 2

The above study was repeated with 28 patients. In contrast to Study 1, no spray according to Example 3 was used. The results of Study 1 were confirmed. Healing was achieved in all patients. Again, it was observed that patients using both microemulsions from Examples 1 and 2 showed a faster healing due to the use of biotin that accelerated nail growth.

However, when comparing the results from Study 2 with those of Study 1, it was noted that healing took slightly longer when the patients omitted cleaning their foot with the spray according to Example 3. This indicates that cleaning the foot with the spray of Example 3 may protect the nails from getting infected again with dermatophytes from the skin of the foot.

Example 7: Treatment of Psoriasis

The microemulsion of Example 4 was tested with 7 patients suffering from psoriasis. The microemulsion of Example 4 was applied twice daily by spraying it directly to an affected skin area for a period of 28 days. Three patients had psoriatic plaques on the knees and elbows. The four other patients had psoriatic plaques on the breast, arm or lower leg. All patients were examined every week.

Results: A significant improvement was observed in all psoriasis patients after the 28-days treatment period. Some patients showed an improvement already after 12 days of treatment. Upon treatment, the treated skin areas showed decreased signs of inflammation, redness and less itching compared to adjacent untreated areas in the same patient. After 28 days of treatment, the plaques were almost completely disappeared.

Example 8: Treatment of Atopic Eczema

The microemulsion of Example 4 was tested with 8 patients suffering from atopic eczema. The microemulsion of Example 4 was applied twice daily by spraying it directly on an affected skin area for a period of 30 days. The patients had eczema in the crook of the arm, on the breast, back and thighs. All patients were examined twice a week.

Results: Less itching was observed in most patients already after the first application of the spray. After three weeks, redness of the affected skin areas was markedly decreased and the majority of the open lesions were healed.

Example 9: Treatment of Scalp Eczema

The microemulsion of Example 4 was tested with 5 patients suffering from eczema on the scalp. The microemulsion of Example 4 was applied once daily by spraying it directly to the scalp.

Results: Itching and lesions disappeared already after a single application of the microemulsion in 4 patients while the remaining patient required a second application.

The invention claimed is:

1. Pharmaceutical composition in the form of a microemulsion, comprising
    (a) from about 2.0 to about 10.0% (w/w) of an alcohol ethoxysulfate;
    (b) from about 5.0 to about 45.0% (w/w) of an ethoxylated glyceryl fatty acid ester; and
    (c) from about 4.0 to about 25.0% (w/w) of an ethoxylated sorbitol or sorbitol anhydride fatty acid ester.

2. Pharmaceutical composition according to claim 1, wherein said alcohol ethoxysulfate is dodecyl alcohol ethoxysulfate.

3. Pharmaceutical composition according to claim 1, wherein said alcohol ethoxysulfate is present in the composition in an amount of 5% to 10.0% (w/w).

4. Pharmaceutical composition according to claim 1, wherein said ethoxylated glyceryl fatty acid ester is an ethoxylated glyceryl cocoate.

5. Pharmaceutical composition according to claim 1, wherein said ethoxylated glyceryl fatty acid ester is present in the composition in an amount of 5% to 20.0% (w/w).

6. Pharmaceutical composition according to claim 1, wherein said ethoxylated sorbitol or sorbitol anhydride fatty acid ester is a partial ester with oleic acid.

7. Pharmaceutical composition according to claim 1, wherein said ethoxylated sorbitol or sorbitol anhydride ester is present in the composition in an amount of 5% to 10.0% (w/w).

8. Pharmaceutical composition according to claim 1, wherein said composition has a pH of 2.5 to 6.5.

9. Pharmaceutical composition according to claim 1, wherein said composition is formulated for topical application.

10. Pharmaceutical composition according to claim 1, wherein said composition further comprises urea.

11. A method for treating a fungal infection of the skin or nail comprising applying a pharmaceutical composition according to claim 1 to an area of skin or nail.

12. The method according to claim 11, wherein said fungal infection of the nail is onychomycosis.

13. The method according to claim 11, wherein said fungal infection of the skin is selected from the group consisting of ringworm, *Tinea cruris, Tinea capitis* and *Tinea pedis*.

14. A method for treating an inflammatory skin disease comprising applying a pharmaceutical composition according to claim 1 to an area of skin.

15. The method according to claim 14, wherein said inflammatory skin disease is psoriasis or atopic eczema.

16. Pharmaceutical composition according to claim 1, wherein said alcohol ethoxysulfate is sodium lauryl ether sulfate.

17. Pharmaceutical composition according to claim 1, wherein said ethoxylated glyceryl fatty acid ester is PEG-7 glyceryl cocoate.

18. Pharmaceutical composition according to claim 1, wherein said ethoxylated sorbitol or sorbitol anhydride fatty acid ester is polysorbate 80.

19. Pharmaceutical composition according to claim 1, comprising
   (a) from about 2.0 to about 10.0% (w/w) sodium lauryl ether sulfate;
   (b) from about 5.0 to about 45.0% (w/w) PEG-7 glyceryl cocoate; and
   (c) from about 4.0 to about 25.0% (w/w) polysorbate 80.

* * * * *